US008632064B2

(12) United States Patent
Salisbury, Jr. et al.

(10) Patent No.: US 8,632,064 B2
(45) Date of Patent: Jan. 21, 2014

(54) POSITIONING APPARATUS WITH LOCKABLE JOINTS AND METHOD OF USE

(75) Inventors: J. Kenneth Salisbury, Jr., Mountain View, CA (US); Joan Savall, Palo Alto, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 1161 days.

(21) Appl. No.: 12/503,727

(22) Filed: Jul. 15, 2009

(65) Prior Publication Data

US 2011/0015647 A1    Jan. 20, 2011

(51) Int. Cl.
*B23Q 1/25*    (2006.01)
*B25B 1/22*    (2006.01)
*B23Q 3/18*    (2006.01)

(52) U.S. Cl.
USPC ................ 269/55; 269/71; 269/75; 269/600; 269/8

(58) Field of Classification Search
USPC ......... 269/71, 75, 60, 55, 8; 414/680; 901/28, 901/29; 384/192, 203, 206, 209, 211; 403/53; 74/490.01, 490.05, 490.06; 62/27
See application file for complete search history.

(56) References Cited

U.S. PATENT DOCUMENTS

| | | | |
|---|---|---|---|
| 4,455,910 A | 6/1984 | Kraft et al. | |
| 4,461,463 A | 7/1984 | Okubo | |
| 4,934,671 A | 6/1990 | Laninga et al. | |
| 6,240,799 B1 | 6/2001 | Yau | |

(Continued)

FOREIGN PATENT DOCUMENTS

| | | |
|---|---|---|
| EP | 0568120 A2 | 11/1993 |
| JP | 57-197620 A | 12/1982 |

(Continued)

OTHER PUBLICATIONS

Bal-tec: Magnetically preloaded kinematic couplings; www.precisionballs.com/magnet_preload.php; 5 pgs.; accessed Nov. 5, 2009.

(Continued)

*Primary Examiner* — Monica Carter
*Assistant Examiner* — Nirvana Deonauth
(74) *Attorney, Agent, or Firm* — ShayGlenn LLP (57) ABSTRACT

A positioning system having a base, a manually movable end effector and a first joint interposed between the base and the end effector is disclosed. The first joint may comprise a proximal portion and a distal portion coupled together by magnetic attraction and configured to be intermittently separated by a pressurized gas cushion. The first joint may be configured to be changeable between a movable state and a fixed state. In the movable state, the proximal and distal portions are separated by the pressurized gas cushion and are movable relative to each other. In the fixed state, the proximal and distal portions contact each other and relative movement is thereby impeded.

Methods of precisely positioning an end effector may include providing a device having a base, a first joint located distally from the base, and an end effector located distally from the first joint. The first joint may have two portions separated by a gas cushion, the first joint allowing the end effector to be movable with respect to the base. The method may further comprise manually positioning the end effector, and removing the gas cushion to cause the two joint portions to contact each other, thereby locking the end effector in the precise location in which it was positioned.

27 Claims, 11 Drawing Sheets (56) References Cited

U.S. PATENT DOCUMENTS

| | | | |
|---|---|---|---|
| 7,445,409 B2* | 11/2008 | Trice et al. | 407/119 |
| 7,686,287 B2* | 3/2010 | Dixon et al. | 269/75 |
| 2004/0195988 A1 | 10/2004 | Buckingham et al. | |
| 2005/0087034 A1 | 4/2005 | Friedrich et al. | |
| 2007/0151117 A1* | 7/2007 | McMurtry | 33/558.2 |
| 2009/0145443 A1* | 6/2009 | Dreyfuss | 128/845 |

FOREIGN PATENT DOCUMENTS

| | | |
|---|---|---|
| JP | 08-229759 A | 9/1996 |
| WO | WO03/007345 | 1/2003 |
| WO | WO-2006/048097 A1 | 5/2006 |

OTHER PUBLICATIONS

Bal-tec: Manufacturer of precisionballs, ball bars, and kinematic components; www.precisionballs.com; 2 pgs.; accessed Nov. 5, 2009.

Hammer et al.; Design and control of an air-bearing supported three degree-of-freedom fine positioner; Proc. 1992 IEEE Int. Conf. on Robotics and Automation; Nice, France; pp. 677-684; May 1992.

Loadpoint Bearings Ltd.; "How Air Bearings Work"; www.loadpoint-bearings.co.uk/products/how_air_bearings_work/; 6 pgs.; accessed Sep. 3, 2009.

Nelson Air Corp.; "Air Bearing Basics"; www.nelsonair.com/NA_primer.htm; 4 pgs.; accessed Sep. 3, 2009.

NewWay Air Bearings; product page; www.newwayairbearings.com/Products; 1 pg.; accessed Sep. 3, 2009.

Ro et al.; Development of a miniature air-bearing stage with a moving-magnet linear motor; Int'l J. Korean Soc. Precision Eng.; pp. 19-24; 2008.

Manrique et al.; Atraumatic Surgical Approach to the Cochlea with a Micromanipulator; Acta Oto-Laryngologica.; vol. 127; No. 2; pp. 122-131; Feb. 2007.

Savall et al.; Micromanipulator for Enhancing Surgeon's Dexterity in Cochlear Atraumatic Surgery; In Proc. of the 28th Ann. Int'l Conf. of the IEEE Eng. in Eng. in Med. And Biology Soc. (EMBS); NY, NY; pp. 335-338; Aug. 20-Sep. 3, 2006.

* cited by examiner

POSITIONING APPARATUS WITH LOCKABLE JOINTS AND METHOD OF USE

FIELD OF THE INVENTION

This invention generally relates to precise positioning devices, in particular articulating devices that can be moved into a particular configuration and accurately locked in that orientation.

BACKGROUND OF THE INVENTION

The need to precisely position a device occurs in many fields of endeavor. One such field is surgery, in which an instrument may need to be precisely positioned relative to a patient undergoing an operation or diagnostic procedure. For example, there is a need to enable an ear surgeon, such as an otologist, to precisely position and manipulate instruments in an around the structures of the ear, particularly the inner and middle ear.

Other more general medical applications of precise positioning devices include those that enable medical personnel to adjustably position imaging, therapeutic, and other instruments at desired locations in and near a patient's body. Such positioning needs arise in ophthalmic, neurological, orthopedic and other medical fields. Even more generally, requirements for precise positioning of an object frequently occur in the field of optics, measurement and manufacturing.

What is desirable, and not provided by prior art methods and devices, is a means for precisely positioning an object in a particular orientation with a support mechanism, and accurately fixing the object in that orientation.

SUMMARY OF THE INVENTION

According to aspects of the present description, a support device may comprise one or more movable links interconnected by selectively lockable joints. The selectively lockable joints allow the linkage mechanism to be manually or otherwise moved to a desired configuration or position while the joints are unlocked, and then to become a partly or fully fixed configuration when some or all of the joints are locked.

In some embodiments, a positioning system comprises a base, a manually movable end effector and a first joint interposed between the base and the end effector. The first joint may comprise a proximal portion and a distal portion coupled together generally by magnetic attraction and configured to be intermittently separated by a pressurized gas or other fluid cushion. The first joint may be configured to be changeable between a movable state and a fixed state. In the movable state, the proximal and distal portions are separated by the pressurized gas cushion and are movable relative to each other in at least one degree of freedom. In the fixed state, the proximal and distal portions contact each other and relative movement is thereby impeded.

In some of the above embodiments, the proximal and distal portions of the first joint may rotate relative to each other in at least two rotational degrees of freedom. The first joint may be a spherical joint. The spherical joint may be capable of movement in three degrees of rotational freedom. In some of the embodiments, the system is configured without a prime mover to position the end effector.

In some of the above embodiments, the system may further comprise a second joint interposed between the base and the end effector in series with the first joint. The second joint may have at least one degree of rotational freedom. Each of the first and second joints may comprise a separately interruptible pressurized gas cushion. In some embodiments, the second joint comprises a proximal portion and a distal portion, and the distal portion of the first joint is coupled to the proximal portion of the second joint by a rigid link. The rigid link may include an internal channel in fluid communication with both the distal portion of the first joint and the proximal portion of the second joint. The rigid link may comprise two or more ends and at least one orifice at each of the ends, wherein each of the orifices is in fluid communication with the internal channel and a gas cushion of one of the joints, and the internal channel may have a cross-sectional area that is larger than the cross-sectional area of each of the orifices in order to create a plenum chamber to store or damp gas flow. In some of these embodiments, the internal channel cross-sectional area is at least four times as large as the lateral cross-sectional area of each of the orifices.

In some embodiments, the system may comprise at least a second joint interposed between the base and the end effector in parallel with the first joint. The first and/or second joints may be spherical, planar, cylindrical or other types of kinematic, joints. In some embodiments, a sphere, planar, cylindrical or other kinematic member serves as a common proximal portion for the first and second joints.

In some embodiments, a positioning system includes at least two parallel links interposed between the base and the end effector. Each of the parallel links may include at least two joints, and each of the joints may be changeable between a movable state and a fixed state.

In some of the above embodiments, the end effector is configured with a lumen for slidably receiving an instrument. In some embodiments, a miniature endoscope instrument may be provided that has a first portion configured to be precisely received within the end effector lumen and a second portion configured for entering a human cochlea. In some of the systems, the base is configured for attaching to a temporal bone.

In some of the above embodiments, the pressurized gas cushion has a thickness of no more than about 50 microns. In other embodiments, the pressurized gas cushion has a thickness of no more than about 5 microns. In still other embodiments, the pressurized gas cushion has a thickness of no more than about 1 micron.

According to aspects of the detailed description, methods of precisely positioning an end effector may include providing a device having a base, a first joint located distally from the base, and an end effector located distally from the first joint. The first joint may have two portions separated by a gas cushion, the first joint allowing the end effector to be movable with respect to the base. The method may further comprise manually positioning the end effector, and removing the gas cushion to cause the two joint portions to contact each other, thereby locking the end effector in the precise location in which it was positioned.

In some of the above methods, the manual positioning step comprises moving the end effector in at least two degrees of rotational freedom. The two portions of the joint may be mutually attracted by a magnetic force. The first joint may be a spherical joint. In some of the methods, the device comprises a second joint located distally from the first joint and proximally from the end effector.

In some of the above methods, the end effector may be positioned in a relatively coarse manner, the gas cushion may be removed from the first joint to lock in the relatively course position of the end effector, the end effector may then be positioned in a relatively fine manner, and then the gas cushion may be removed from the second joint to lock in the relatively fine position of the end effector.

Some methods may include a step of removably attaching the base of the device to a bone of a patient. In some of the above methods, a miniature endoscope is moved relative to the end effector and into a cochlea.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1A:
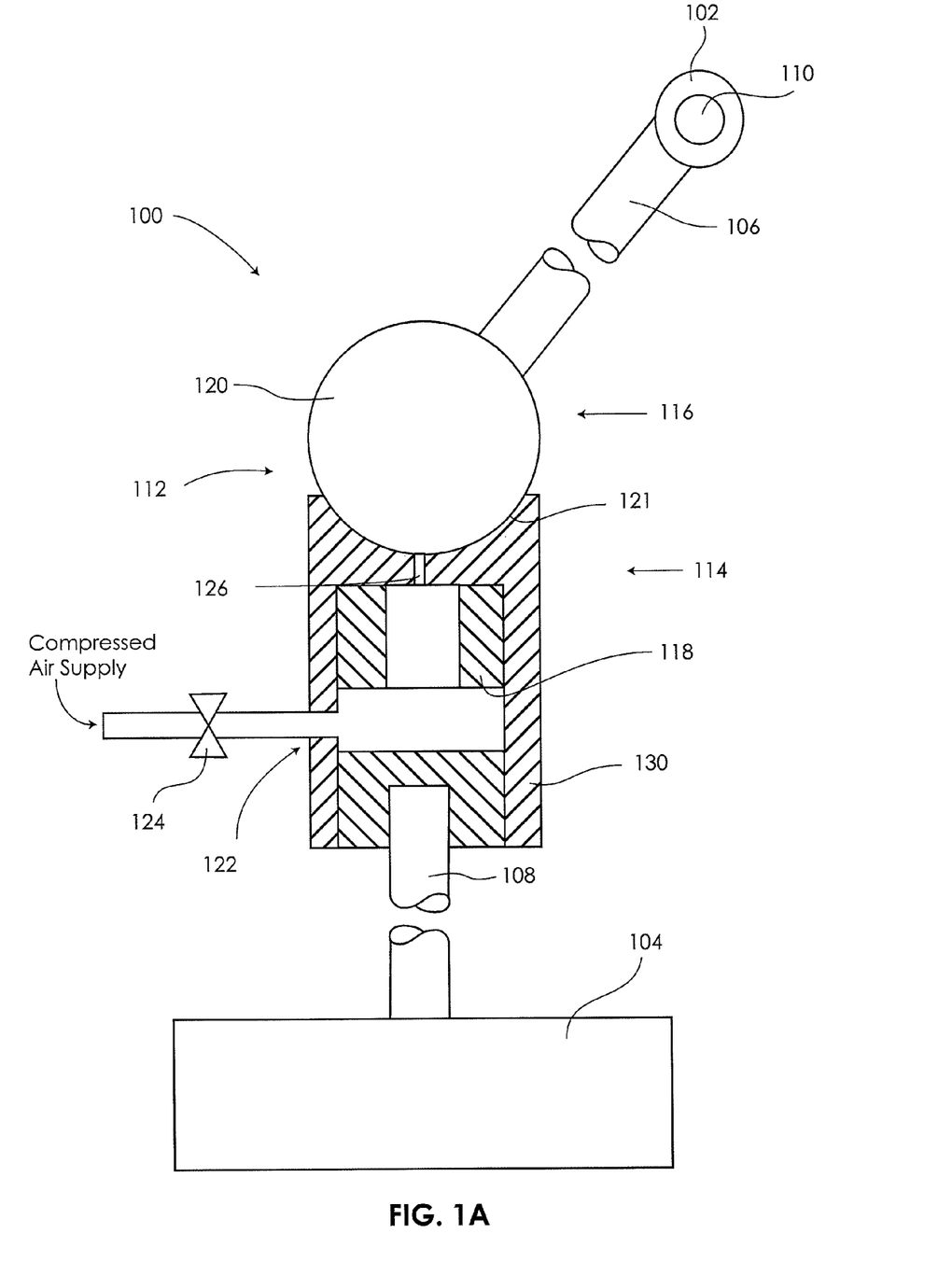
FIG. 1A is a cross-sectional side view showing an exemplary positioning device constructed according to aspects of the Detailed Description and having an articulating joint in a locked or fixed state.

Referring to FIG. 1A, an exemplary positioning device 100 constructed according to aspects of the present invention is schematically shown. Device 100 includes an end effector 102 movably connected to base 104 by articulating links 106 and 108. In this embodiment, end effector 102 includes a through-hole 110 for receiving an object to be positioned (not shown in FIG. 1A). Base 104 may rest on or be attached to a stationary reference surface. In alternative embodiments, base 104 may be coupled to a movable apparatus, such as for coarse positioning of device 100.

In the embodiment shown in FIG. 1A, articulating link 106 is rigidly connected to end effector 102, and articulating link 108 is rigidly connected to base 104. Links 106 and 108 are movably coupled together by joint 112. In this embodiment, joint 112 is a spherical joint comprising a proximal portion 114 located on link 108 and a distal portion 116 located on link 106. Proximal portion 114 comprises an annular magnet 118 fixed within an axial bore of proximal portion 114, such as by a press fit, adhesive, or molded therein. Distal portion 116 of joint 112 includes a spherical member 120. Spherical member 120 comprises a ferrous and/or magnetic material such that it is attracted to magnet 118. In this manner, proximal portion 114 and distal portion 116 of joint 112 are drawn towards each other by magnetic attraction. In this embodiment, proximal portion 114 includes a concave surface 121 having substantially the same radius of curvature as that of spherical member 120, thereby creating intimate contact between substantially all of surface 121 and a portion of the outer surface of spherical member 120. The combination of magnetic force and large surface area contact in this embodiment causes spherical member 120 to be in a locked position relative to proximal portion 114 when in this configuration. As a consequence of this fixed or locked configuration of joint 112, end effector 102 is generally immovable relative to base 104.

Figure 1B:
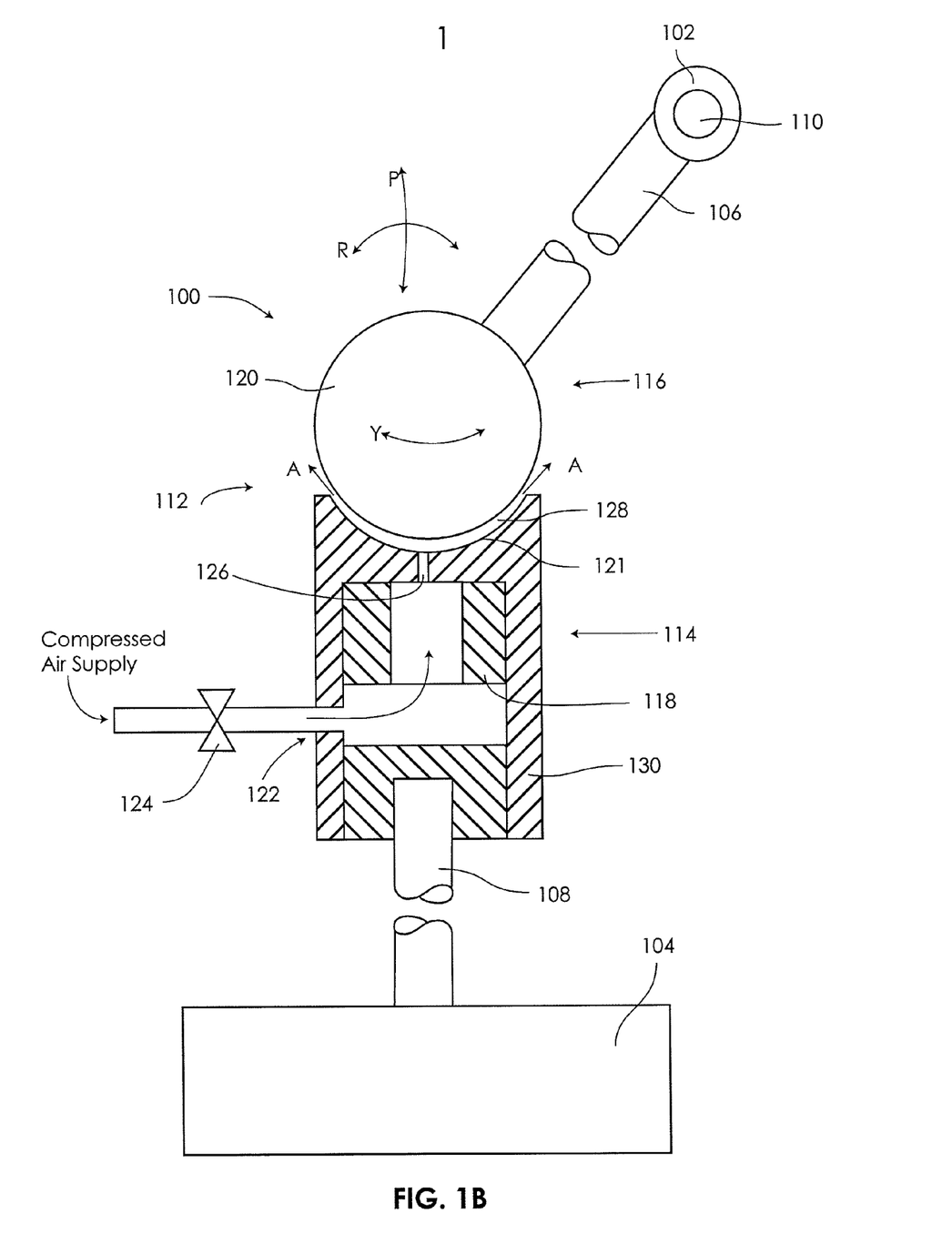
FIG. 1B is a cross-sectional side view showing the positioning device of FIG. 1A with the articulating joint in a movable state.

Referring now to FIG. 1B, proximal portion 114 of joint 112 further comprises an inlet port 122 connected to a compressed air supply (or other compressed gas or fluid supply) by valve 124. Inlet port 122 is in fluid communication with channel 126 through the axial bore of proximal portion 114. Channel 126 is located adjacent to spherical member 120. When valve 124 is opened, compressed air flows from the supply through channel 126 with enough pressure to overcome the magnetic attraction between the proximal and distal portions of joint 112, urging spherical member 120 apart from mating concave surface 121. A thin air cushion 128 is thus formed between spherical member 120 and concave surface 121 as compresses air flows between the two and exits in the direction of the arrows labeled A. The farther that spherical member 120 moves away from concave surface 121, the lower the resulting air pressure between the two surfaces, because the air is allowed to escape more easily. Therefore, the pressurized air will only move spherical member 120 a predetermined distance away from mating surface 121, held in balance by the equal and opposite force of magnetic attraction between magnet 118 and spherical member 120. The strength and location of magnet 118, the pressure of the compressed air (or other gas), the surface area between spherical member 120 and mating surface 121, surface roughnesses, and other parameters may be selected such that air cushion 128 may be kept to a minimal thickness yet allows spherical member 120 to move freely relative to mating surface 121. In some embodiments, air cushion 128 has a thickness of about 5 microns or less.

With the above arrangement, valve 124 may be opened to allow joint 112 to be changed from a fixed state to a movable state by creating an air cushion 128 between the proximal portion 114 and the distal portion 116. When joint 112 is in the movable state, as shown in FIG. 1B, end effector 102 may freely be moved by hand or other means to any desired position. Air cushion 128 allows end effector 102 to be moved with very little friction. Valve 124 may then be closed to remove air cushion 128 and cause proximal portion 114 and distal portion 116 to contact each other, thus changing joint 112 from the movable state to the fixed state, as shown in FIG. 1A. Because the thickness of air cushion 128 may be very small in some embodiments, there is no appreciable movement when joint 112 is changed from the movable state to the fixed state.

In some embodiments, joint 112 may be configured such that it is freely movable when valve 124 is sufficiently open, and movable with some resistance when valve 124 is opened to a lesser extend. In other words, when valve 124 is only partially open, the air cushion formed is sufficient to partially overcome the magnetic attraction between the proximal and distal portions of joint 112, but is not so thick as to provide complete separation between the entirety of the mating surfaces. This arrangement may be desirable when some fixation force is desired to overcome gravity or other small disturbing forces, but still allow the position of end effector 102 to be adjusted before being locked.

In the embodiment shown in FIG. 1B, joint 112 (and therefore also end effector 102) may be moved in three degrees of rotational freedom when in the movable state. These degrees of freedom can be described as roll, pitch and yaw, as depicted by arrows labeled R, P and Y, respectively. In other embodiments (not shown), joint 112 may be constrained to just two or one degrees of freedom.

To increase the holding force between spherical member 120 and mating surface 121 when joint 112 is in the fixed state, one or both of these surfaces may be roughened. This may be accomplished by choice of component material(s), coating the surface(s), and/or various finishing techniques such as sand blasting. In some embodiments, high-friction coatings or base materials may be used to increase friction without adding surface roughness, thereby increasing the precision of the joint. Porous surface materials may also be used to increase performance in both the locked and movable states of the joint.

Figure 1C:
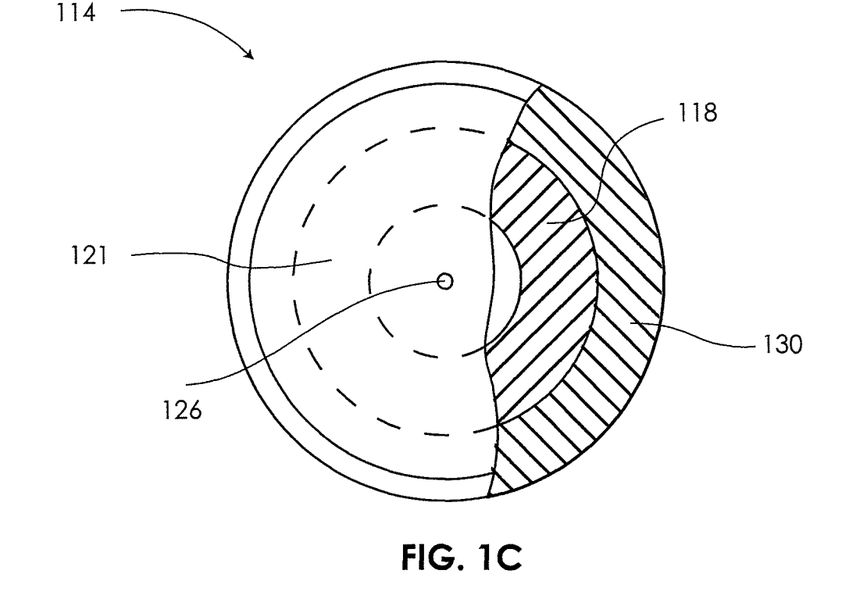
FIG. 1C is a partially broken away plan view showing the proximal portion of the articulating joint shown in FIG. 1A.

Referring to FIG. 1C, a partially broken away axial view of proximal portion 114 is shown, illustrating magnet 118 within the body 130 of proximal portion 114.

Figure 1D:
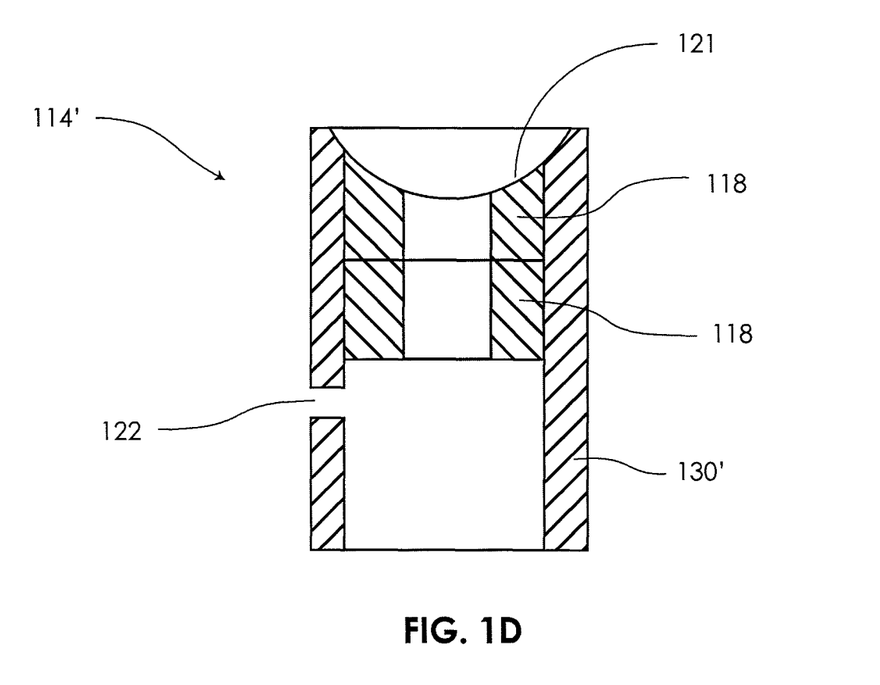
FIG. 1D is a cross-sectional side view showing a variation of the proximal portion of the articulating joint shown in FIG. 1A.

Referring to FIG. 1D, an alternate embodiment of proximal portion 114' is shown. As depicted, two (or more) annular magnets 118 may be axially aligned to provide greater holding strength. Also, the upper magnet need not be embedded below concave surface 121 as in the embodiment shown in FIGS. 1A-1C, but may be fabricated to form part or all of surface 121 itself. Along these lines, an alternate proximal portion (not shown) may be formed from a unitary piece of ferrous and/or magnetic material, such as by sintering, grinding, and/or other fabrication techniques known to those skilled in the art.

Referring now to FIGS. 2A-2D, various views of another embodiment are shown. In this embodiment, small cylindrically-shaped magnets 202 are arranged in an off-axis manner. Three magnets 202 may be equally spaced around the central axis of proximal portion 204 of spherical joint 206. As can best be seen in FIG. 2A, the individual axes of magnets 202 may be generally aligned with the center of spherical member 208. The proximal end 210 of an air channel can be seen in FIGS. 2A-2C, while the distal end 212 of the air channel can be seen in the middle of concave mating surface 214 in FIG. 2D.

Figure 2A:
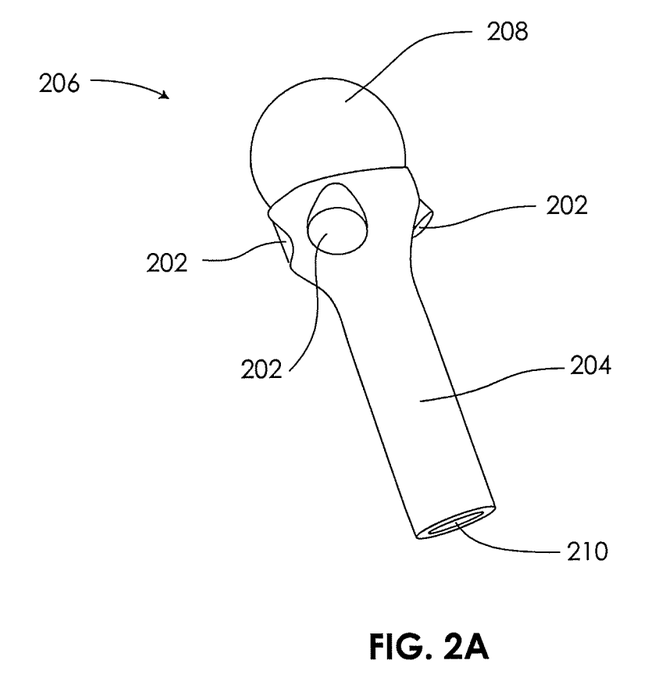
FIG. 2A is a side perspective view showing another embodiment of an articulating joint.
Figure 2B:
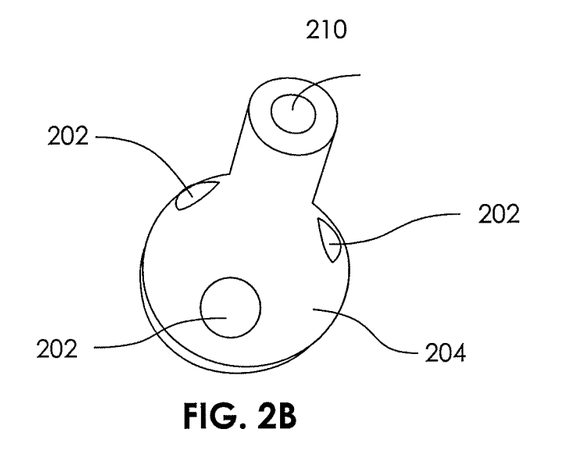
FIG. 2B is a bottom perspective view showing the concave portion of the articulating joint of FIG. 2A.
Figure 2C:
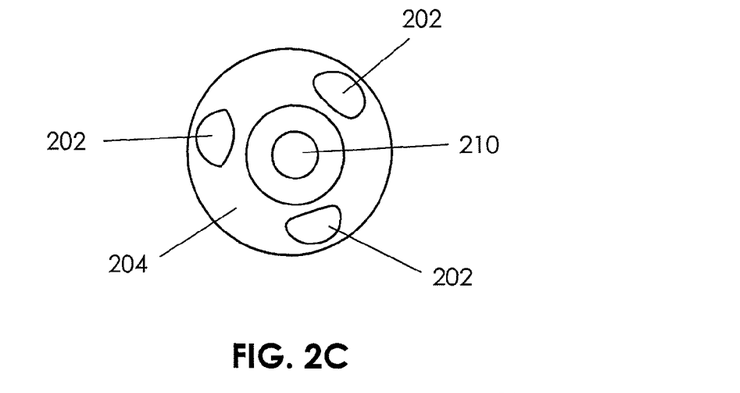
FIG. 2C is a bottom view showing the concave portion of the articulating joint of FIG. 2A.
Figure 2D:
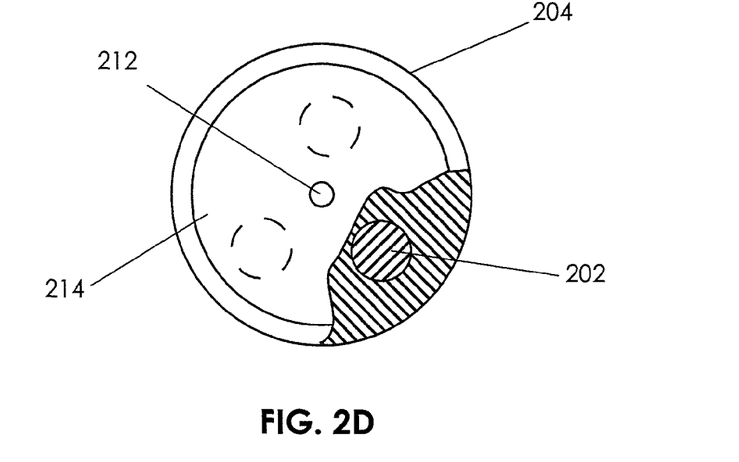
FIG. 2D is a partially broken away top view showing the concave portion of the articulating joint of FIG. 2A.
Figure 2E:
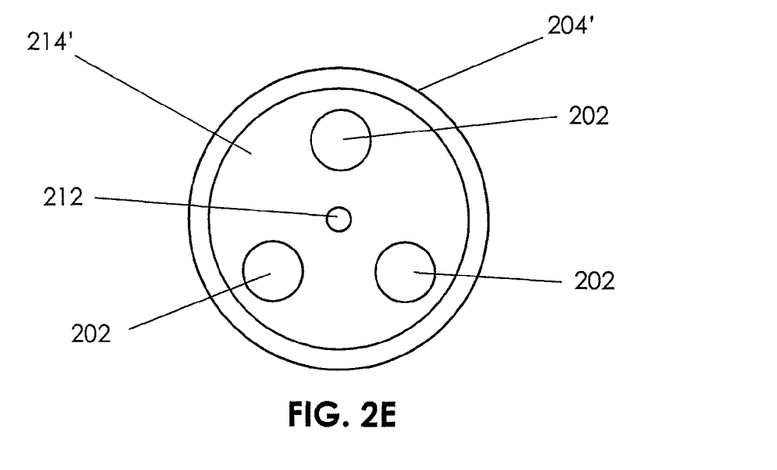
FIG. 2E is a top view showing a variation of the concave portion of the articulating joint of FIG. 2A.

Referring to FIG. 2E, a variation of the embodiment of FIG. 2A-2D is shown. In this embodiment, magnets 202 protrude through concave spherical surface 214' rather than being embedded below the surface. Magnets 202 may stand proud of surface 214', be flush with it, or be slightly recessed. In some embodiments, the body of proximal portion 204' may be fabricated by placing magnets 202 on spherical member 208 in a desired spacing, placing spherical member 208 with attached magnets 202 at least partially into a mold cavity, and filling the mold cavity with a hardenable substance around magnets 202, such as with a thermoplastic, thermosetting plastic, resin or epoxy. Once the substance has hardened, spherical member 208 may then be separated from magnets 202 and the hardenable substance (a mold release may need to be applied to spherical member 208 before molding), leaving the concave mating surface 214 and magnets as shown in FIG. 2E.

In some embodiments (not shown), the distal end 212 of the air channel may be made larger, and/or a network of shallow grooves in fluid communication with the distal end 212 of the air channel may be provided along concave surface 214. This arrangement provides a larger area of the pressurized air when it is first activated to move spherical member 208 away from magnets 202. Accordingly, a lower pressure air supply may be used for a given magnet arrangement, and oscillations of the spherical member 208 when first separated from magnets 202 may be avoided.

In some embodiments, fewer or more than the three magnets 202 shown in FIGS. 2A-2E are used. High energy magnets may be used to allow for a greater magnetic attraction force in a smaller package.

In some embodiments, the positions of the ball and socket members are reversed. In other words, spherical member 120 or 208 may be located on the proximal portion of the articulating link and mating concave surface 121 or 214 may be located on the distal portion, opposite of the arrangement shown in FIGS. 1A and 1B. In some embodiments, the base may be located beside or above the end effector, mounted at an angle, and/or mounted on a movable platform.

While only spherical articulating joints have been discussed up to this point, it is to be understood that other types of kinematic joints may be used to form bearing and braking mechanisms. For example, using the concepts described above, a revolute joint may be constructed (one degree of freedom), or a prismatic joint (one degree of freedom), a cylindrical joint (two degrees of freedom), a planar joint (two or three degrees of freedom), or a spherical joint (with up to three degrees of freedom). Combinations of these joints may also be used in series and/or parallel, as will be described in more detail below. In general, each joint may be formed by a pair of surfaces that have congruent areas of contact.

Figure 3A:
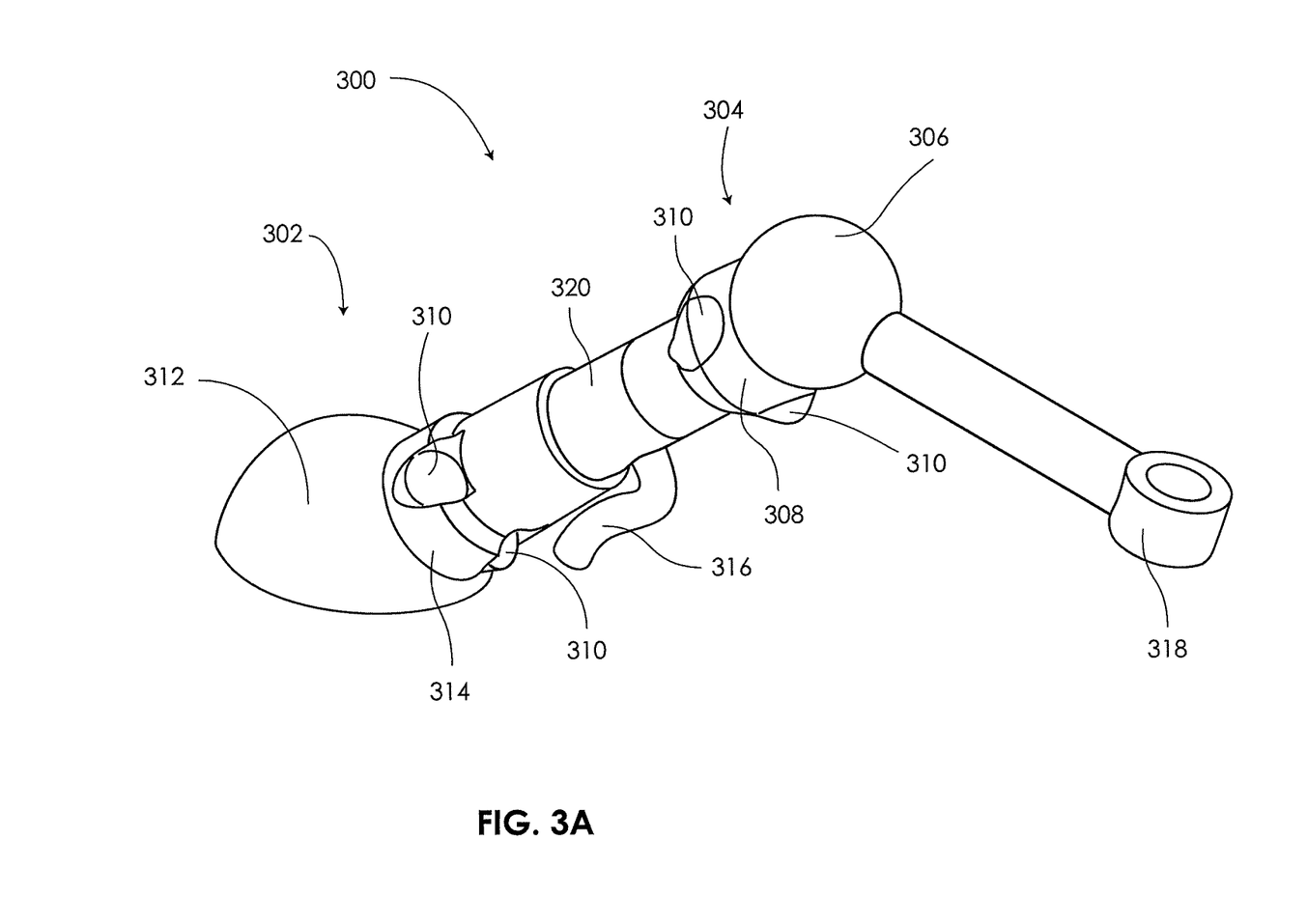
FIGS. 3A-3D are various perspective views showing alternative embodiments of positioning systems having one or more pairs of lockable articulating joints.

Referring to FIG. 3A, a positioning apparatus 300 is shown having two articulating joints 302 and 304 in series. Joint 304 is similar to those previously described, having a spherical member 306 forming its distal portion, and a mating concave member 308 with magnets 310 forming its proximal portion. Joint 302 has a similar construction, with a larger spherical member 312 forming its proximal portion, and a mating concave member 314 with magnets 310 forming its distal portion. A single air supply 316 may be used to simultaneously activate both joints 302 and 304. When compressed air is introduced through common air supply 316, a thin air cushion is formed between spherical member 306 and mating concave member 308, and also between spherical member 312 and mating concave member 314. Each of the two air cushions allows one of the articulating joints 302 and 304 to move in up to three degrees of freedom, thereby allowing the mechanism to move in up to six degrees of freedom.

In the embodiment shown in FIG. 3A, articulating joints 302 and 304 are separated by a rigid link 320. An internal air channel (not shown) running longitudinally within link 320 delivers compressed air from common air supply 316 to each of the two joints 302, 304. In some embodiments, this internal air channel is formed by a bore of constant diameter extending between an office in the concave member 308 of joint 302 and an orifice in the concave member 314 of joint 304, and having the same diameter as the two orifices. In other embodiments, it may be desirable to maximize the diameter of the internal air channel, or to otherwise provide a plenum between joints 302 and 304. Such arrangements can avoid oscillations that may otherwise occur in joints 302 and 304. In some embodiments, the internal channel has a minimum lateral cross-sectional area that is at least four times as large as a lateral cross-sectional area of each of the orifices. In some embodiments, the internal channel has a maximum lateral cross-sectional area that is at least one-half as large as a minimum total lateral cross-sectional area of link 320.

Figure 3B:
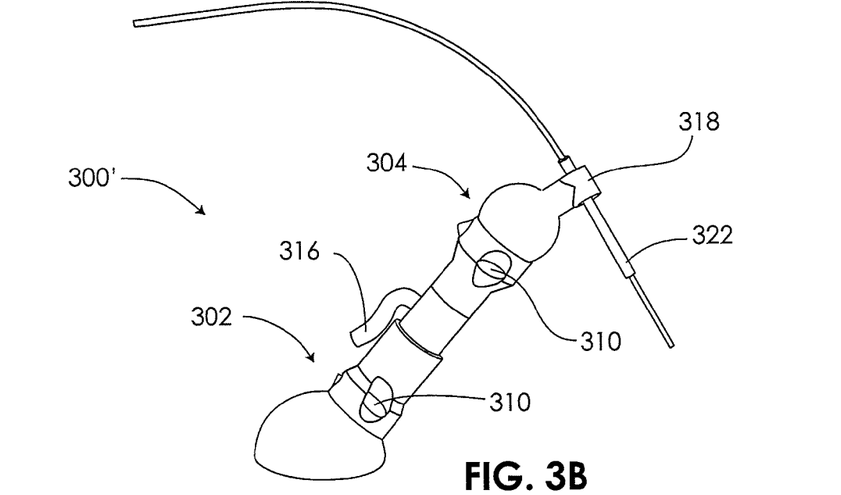

Referring to FIG. 3B, a positioning apparatus 300' similar to positioning apparatus 300 shown in FIG. 3A. Apparatus 300' includes an instrument 322 that may be slidably received in a lumen within end effector 318. Instrument 322 may be medical device, such as miniature endoscope having a first portion configured to be precisely received within the end effector lumen and a second portion configured for entering a human cochlea.

In operation, compressed air may be supplied to common supply 316 as previously described, allowing joints 302 and 304 to freely articulate. It should be noted that the arrangement of positioning apparatus 300' allows instrument 322 to remain in a particular orientation if desired as it is moved laterally and/or longitudinally in three dimensions. Once instrument 322 has been positioned and oriented as desired, the air supply to joints 302 and 304 may be interrupted. This allows magnets 310 to lock joints 302 and 304, thereby holding instrument 322 precisely in place. In other embodiments, the air supply to joints 302 and 304 may be independently controlled, allowing only one joint to be locked while the other joint is still free to move.

Figure 3C:
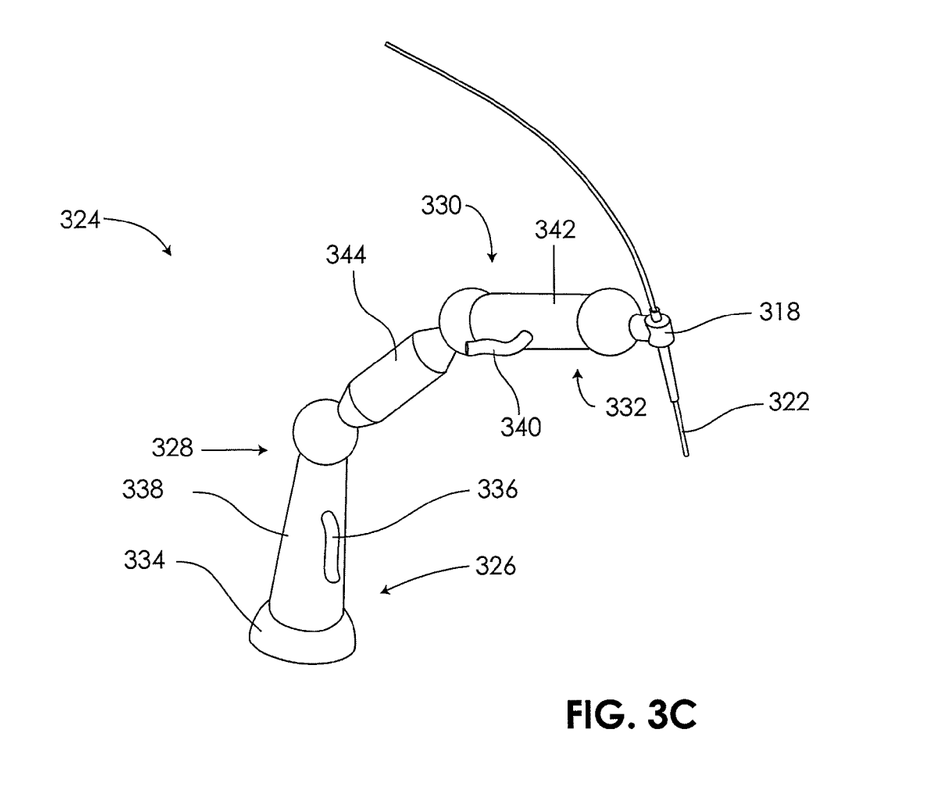

Referring to FIG. 3C, another embodiment of a positioning system is shown. Positioning system 324 includes four articulating joints 326, 328, 330 and 332 connected in series between base 334 and end effector 318. In this embodiment, each joint is a spherical joint that is changeable between a movable state and a fixed or locked state, similar to those previously described. Joints 326 and 328 share a first common compressed air supply line 336 within link 338. Joints 330 and 332 share a second common compressed air supply line 340 within link 342. Joints 328 and 330 are spaced apart by link 344.

First supply line 336 and second supply line 340 may be connected to a single control valve (not shown) such that all four joints 326, 328, 330 and 332 are either in a movable state or a locked state at the same time. Alternatively, the first and second supply lines 336 and 340 may be independently controlled. In this manner, the coarse positioning of instrument 322 may be obtained with all four joints, or at least joints 326 and 328 being in the movable state. Joints 326 and 328 may then be locked in position by turning off the air supply to first common supply line 336. Joints 330 and 332 may be left in the movable state so that fine positioning of instrument 322 may be performed. The air supply to second common supply line 340 may then be turned off to fully lock the position of instrument 322. To control one or both of the air supply lines 336 and 340, manually or electrically actuated valve(s) may be used. To further control the valves, foot pedals, electronic switches, and/or electronic or mechanical controllers may be used. The foot pedal(s) and/or electronic switches may control the air supply in a binary fashion such that it is either fully on or fully off, or may allow variable control so that the air supply may be gradually turned on or off In other embodiments, two, three, four or more articulation joints may be independently controlled.

Figure 3D:
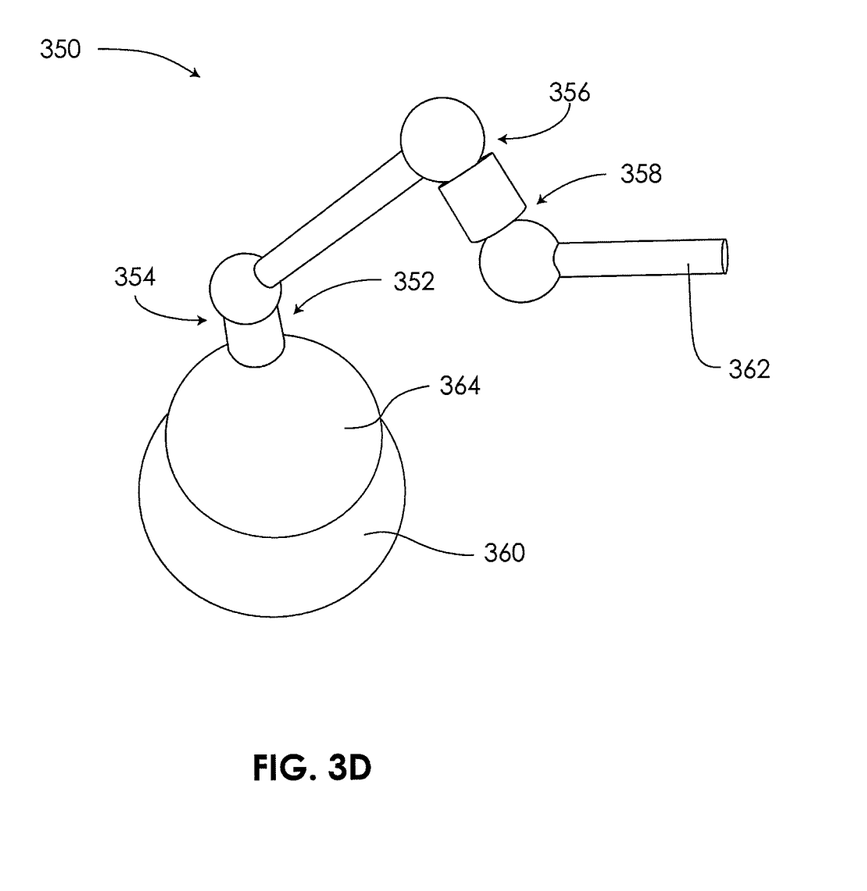

Referring to FIG. 3D, another embodiment of a positioning system is shown. Positioning system 350 includes four articulating joints 352, 354, 356, and 358 connected in series between base 360 and end effector 362. In this embodiment, the proximal portion of joint 352 includes a large spherical member 364 rigidly attached to base 360. In other embodiments, spherical member 364 may form a movable and lockable joint with base 360.

Figure 4A:
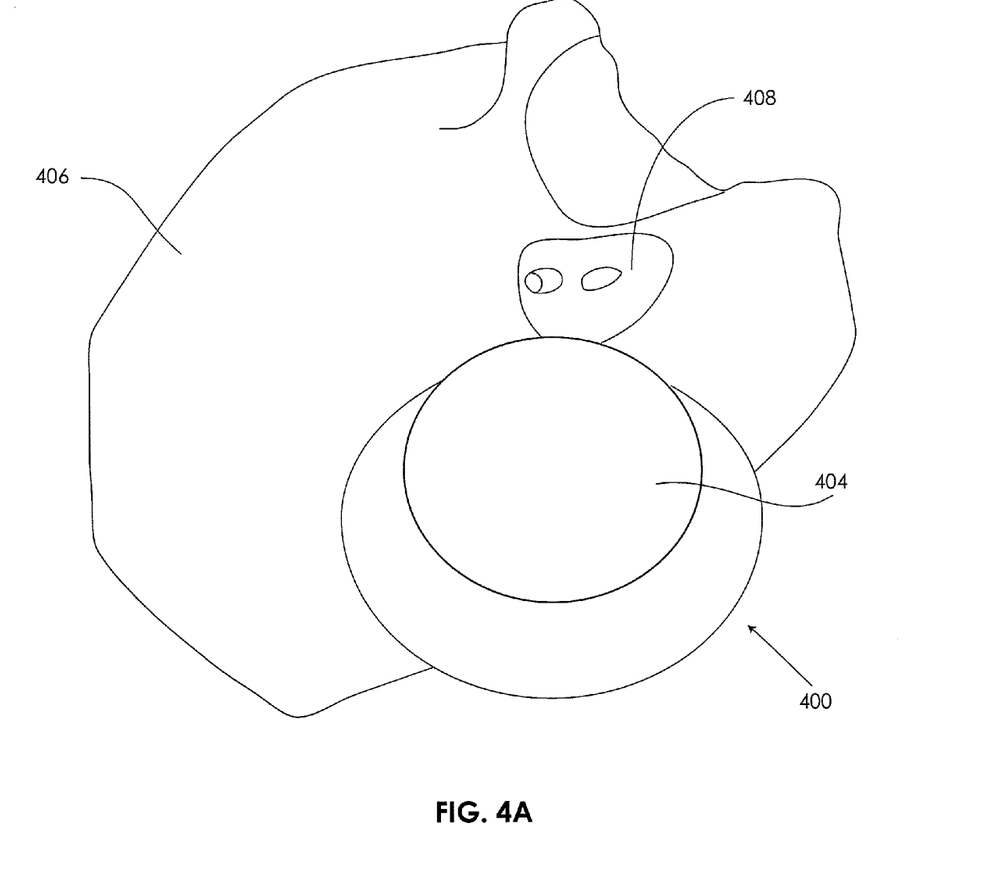
FIGS. 4A-4C are various perspective views showing an embodiment of a positioning system mounted on a templar bone and having joints in series and in parallel.
Figure 4B:
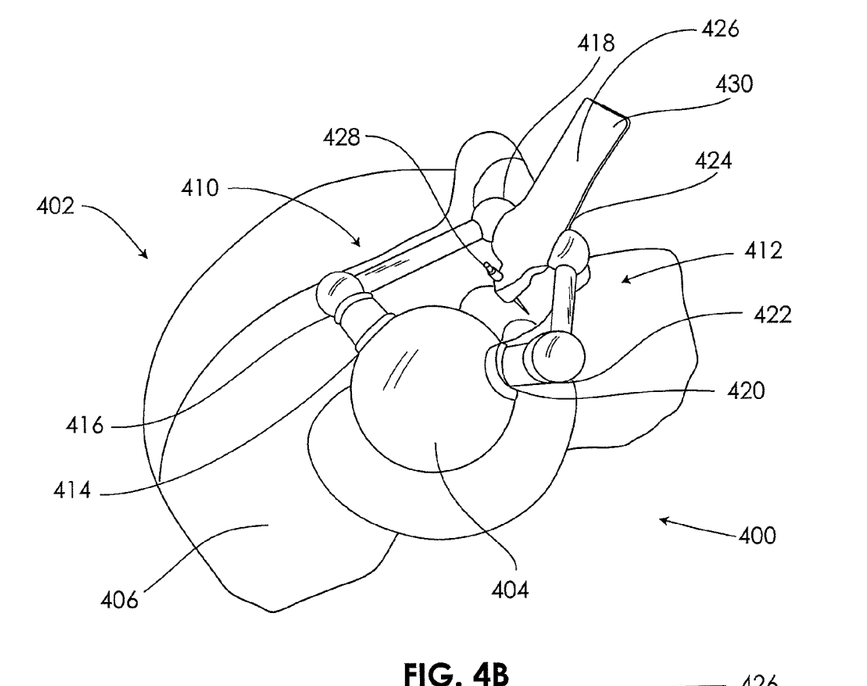
Figure 4C:
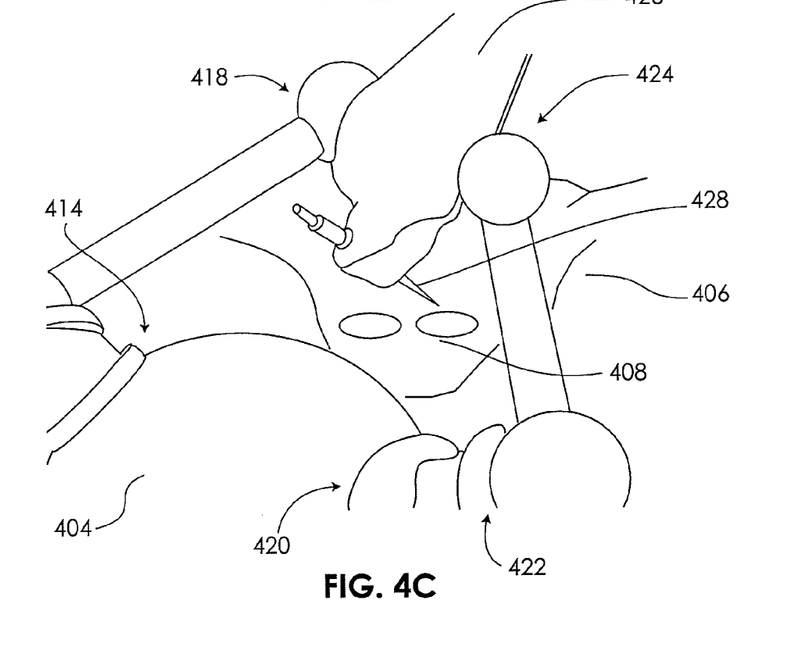

Referring to FIGS. 4A-4C, another embodiment of a positioning system is shown. FIG. 4A shows the base 400 of system 402. Base 400 includes a large spherical member 404, similar to base 360 shown in FIG. 3D. Base 400 is shown attached to a temporal bone 406 adjacent to the external acoustic meatus 408 of the ear canal. Attachment may be made using one or more bone screws (not shown) passing through or formed in base 400 and temporarily extending into the temporal bone 406. Such a mounting on bone provides a secure base from which to precisely position an instrument with system 402, such as a miniature endoscope for insertion into the cochlea as previously described.

FIGS. 4B and 4C show the articulating joints of positioning system 402. In this exemplary embodiment, system 402 includes a first series 410 of articulating joints and a second series 412 of articulating joints. The first series 410 includes joints 414, 416 and 418. The second series includes joints 420, 422 and 424. Spherical member 404 serves as a common proximal portion for both joints 414 and 420. When in the movable state, the distal, concave portion of each of joints 414 and 420 may move across spherical member 404. End effector 426 includes a section that serves as a common distal portion for both joints 418 and 424. In this arrangement, the first and second series 410 and 412 of joints are arranged in parallel to connect end effector 426 with base 400. With two series of joints arranged in parallel as shown in this example, end effector 426 may be held more stably while still being able to be positioned in a wide range of positions and orientations.

End effector 426 also includes a section for receiving an instrument 428, such as a miniature endoscope, and a handle section 430 for manually manipulating the position and orientation of instrument 428 when the articulating joints are in their movable state.

Using the joint construction of the previously described exemplary embodiments, there is little movement of the joints when they are changed from there movable state to their fixed state. In many embodiments, this movement is less than 5 microns (the thickness of the air cushion between the parts of the joint.) This very small movement may become even more important when six or more joints are used in combination as shown. This inventive arrangement allows an instrument to be precisely positioned, and then locked firmly in place without significant movement occurring during the locking of the joints.

In other embodiments, any number or type of articulating joints may be arranged in series, parallel or both to form lockable, precision positioning systems similar to those described above.

In some embodiments (not shown), one or more joints may be formed with pairs of magnets aligned in such a way that the magnetic attraction between the opposing magnets provides a self centering effect. For example, instead of using a ferrous sphere as one portion of a lockable joint, a sphere having magnet(s) or ferrous portion(s) aligned with magnet(s) on the concave portion of the joint can be used, causing the joint to seek a particular orientation of the sphere relative to the concave portion. This type of arrangement can be used to at least partially overcome the effects of gravity or other disturbing forces when the joint is in the movable state.

In some embodiments, an electromagnet can be provided in the articulating joint(s). The electromagnet may be energized to lock the joint without interrupting the air flow, or may be used to increase the frictional engagement of the joint when locked.

In some embodiments, vacuum between the two portions of a joint may be used to further lock the joint from movement.

In some embodiments, the joint can be configured to act as a mechanical fuse for overload protection. By properly selecting the characteristics of both sides of a joint, the joint can be designed to come apart when a predetermined load is reached. This can protect other parts of the positioning system from being damaged by excessive loading.

Figures 5A, 5C:
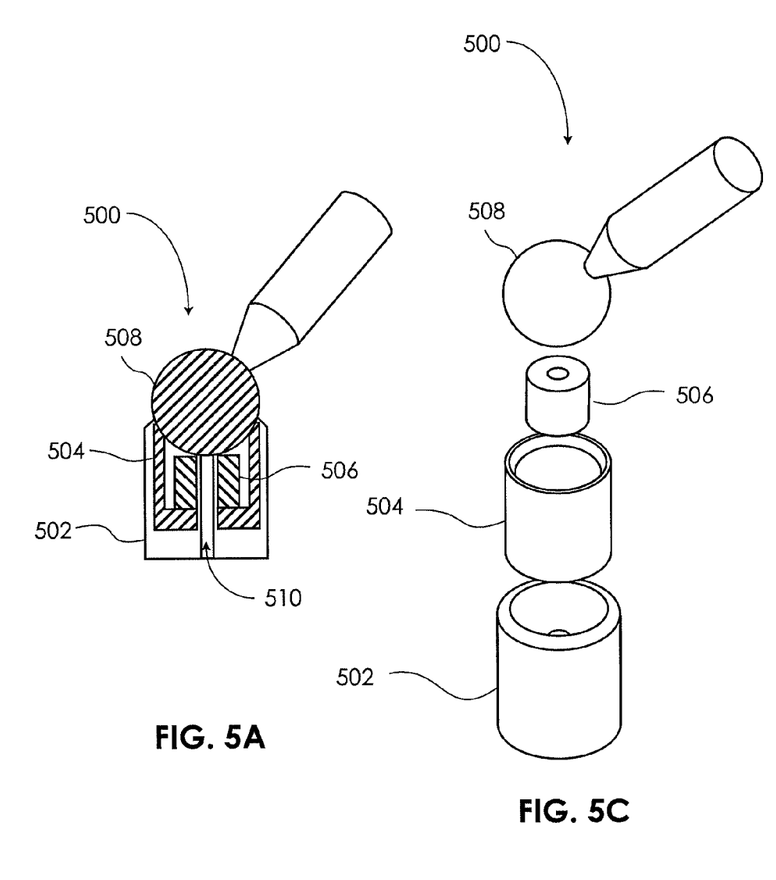
FIG. 5A is a cross-sectional side view showing an alternative embodiment of an articulating joint.
FIG. 5C is an exploded perspective view showing the articulating joint of FIG. 5A.
Figure 5B:
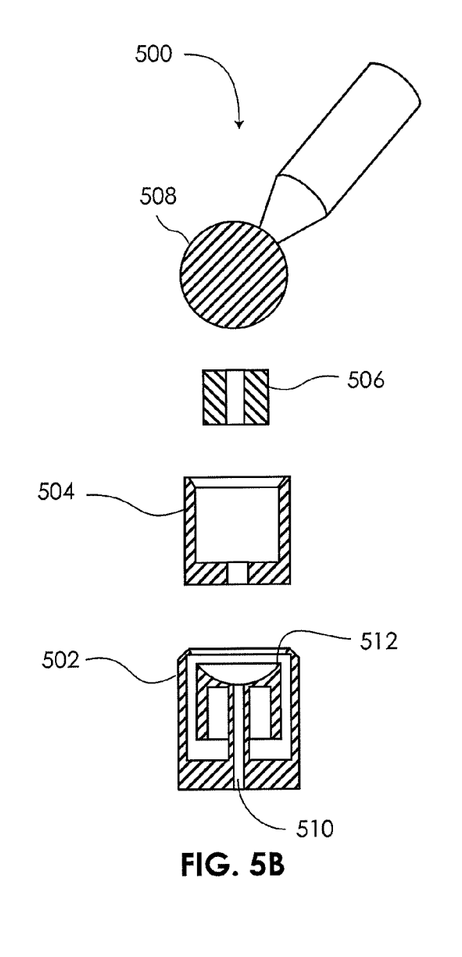
FIG. 5B is an exploded cross-sectional side view showing the articulating joint of FIG. 5A.

Referring to FIGS. 5A-5C, an alternative embodiment articulating joint 500 is shown. In this exemplary embodiment, joint 500 includes a plastic housing 502, a ferromagnetic liner 504, a permanent magnet 506, and a steel ball 508. As best seen in FIG. 5A, liner 504 is cup shaped and is received within housing 502. Magnet 506 is received within liner 504 and resides between the bottom of liner 504 and steel ball 508 when joint 500 is assembled. An axial lumen 510 is provided in housing 502 that extends through liner 504 and magnet 506 to allow compressed air to be supplied between ball 508 and a mating concave surface 512 formed in housing 502.

With the above arrangement, an effective connection can be made between both poles of magnet 506 (the top and bottom surfaces in this embodiment) and steel ball 508. This completes the magnetic circuit between magnet 506 and steel ball 508 and significantly reduces the air gap between the two, thereby reducing the reluctance of the magnetic circuit. Such an arrangement can serve to increase the attractive force between magnet 506 and ball 508. It can also minimize the magnetic influence between neighboring joints, thereby reducing undesirable attractive and/or repulsive forces from one joint on another.

In other embodiments, a ferromagnetic body can be used in a similar manner to optimize magnetic flux. For example, in embodiments having planar joints (not shown), a ferromagnetic body with a particular configuration can be added to the joint to allow a magnetic circuit to be completed between both poles of a magnet in one side of the joint and a ferrous material located in the other side of the joint.

In some embodiments, multiple instruments may be located at the distal end and/or at intermediate positions along the length of the articulating positioning system. For example, a surgical instrument may be located at the distal end, a suction device may be located at link proximal to the surgical instrument, and a lighting apparatus may be located at a link proximal to the suction device. In use, the more proximal link holding the lighting apparatus may be positioned and locked first, then the suction device link may be positioned and locked, and then the surgical instrument may be positioned and locked.

While exemplary embodiments constructed according to aspects of the present invention have been shown and described herein, it will be obvious to those skilled in the art that such embodiments are provided by way of example only. Numerous variations, changes, and substitutions will now occur to those skilled in the art without departing from the invention. For example, other means of inducing attractive forces between bodies may be used including electromagnets, springs, capacitive and electrostatic forces, as well as other nuclear and inertial effects that give rise to force. Surface materials, textures, porosities and geometries may be selected to increase friction in the locked state. As an example of surface geometries that may be used, mating splines may be located on opposing portions of a joint to lock the joint in one of a series of discrete positions when the joint is changed to a fixed state. It should be understood that various alternatives to the embodiments of the invention described herein may be employed in practicing the invention.

What is claimed is:

1. A positioning system comprising:
   a base;
   a manually movable end effector;
   a first joint and a second joint, each interposed between the base and the end effector;
   a first link interposed between the first joint and the base;
   a second link interposed between the first joint and the end effector;
   a third link interposed between the second joint and the base; and
   a fourth link interposed between the second joint and the end effector,
   wherein the second joint, the third link, and the fourth link are together interposed between the base and the end effector in a parallel manner with the first joint, the first link, and the second link to form two separate paths between the base and the end effector, wherein the first and the second links each have a fixed length to keep a fixed distance between the first joint and any adjacent joint, the base or the end effector, wherein the second and the third links each have a fixed length to keep a fixed distance between the second joint and any adjacent joint, the base or the end effector, the first joint and the second joint each comprising a proximal portion and a distal portion coupled together by magnetic attraction and configured to be intermittently separated by a pressurized gas cushion, the first joint and the second joint each configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded, wherein the first link is movable relative to the second link when the first joint is in the movable state, and relative movement between the first and second links is impeded when the first joint is in the fixed state, and wherein the third link is movable relative to the fourth link when the second joint is in the movable state, and relative movement between the third and fourth links is impeded when the second joint is in the fixed state.

2. The system of claim 1, wherein the at least two degrees of freedom of each of the first and the second joints comprise at least two rotational degrees of freedom.

3. The system of claim 1, wherein at least the first joint is a spherical joint.

4. The system of claim 3, wherein the spherical joint is capable of movement in three degrees of rotational freedom.

5. The system of claim 1, wherein the system is configured without a prime mover to position the end effector.

6. The system of claim 1, wherein each of the first and second joints comprises a separately interruptible pressurized gas cushion.

7. The system of claim 1, wherein the first and second joints are both spherical joints.

8. A positioning system comprising:
   a base;
   a manually movable end effector; and
   a first joint and a second joint, each interposed between the base and the end effector, the first joint and the second joint each comprising a proximal portion and a distal portion coupled together by magnetic attraction and configured to be intermittently separated by a pressurized gas cushion, the first joint and the second joint each configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded, wherein the second joint is interposed between the base and the end effector in parallel with the first joint, wherein the first and second joints are both spherical joints, the system further comprising a sphere member that serves as a common proximal portion for the first and second joints.

9. A positioning system comprising:

a base;

a manually movable end effector; and a first joint and a second joint, each interposed between the base and the end effector, the first joint and the second joint each comprising a proximal portion and a distal portion coupled together by magnetic attraction and configured to be intermittently separated by a pressurized gas cushion, the first joint and the second joint each configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded, the system further comprising at least two parallel links interposed between the base and the end effector, wherein each of the parallel links comprises at least two joints, at least one of which is changeable between a movable state and a fixed state.

10. The system of claim 1, wherein the end effector is configured with a lumen for slidably receiving an instrument.

11. A positioning system comprising:

a base;

a manually movable end effector; and a first joint and a second joint, each interposed between the base and the end effector, the first joint and the second joint each comprising a proximal portion and a distal portion coupled together by magnetic attraction and configured to be intermittently separated by a pressurized gas cushion, the first joint and the second joint each configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded, wherein the end effector is configured with a lumen for slidably receiving an instrument, the system further comprising a miniature endoscope instrument having a first portion configured to be precisely received within the end effector lumen and a second portion configured for entering a human cochlea.

12. A method of precisely positioning an end effector, the method comprising:

providing a device having a base, a first joint and a second joint, each of the first and second joints located distally from the base, and the end effector located distally from the first and second joints, the first and second joints each having two portions separated by a gas cushion, the first and second joints allowing the end effector to be movable with respect to the base;

manually positioning the end effector; and removing the gas cushion to cause the two joint portions of each of the first and second joints to contact each other, thereby locking the end effector in the precise location in which it was positioned, wherein the end effector moves no more than about 10 microns when the gas cushion is removed from both of the first and the second joints to lock the end effector.

13. The method of claim 12, wherein the manual positioning step comprising moving the end effector in at least two degrees of rotational freedom.

14. The method of claim 12, wherein the two portions of each of the first and second joints are mutually attracted by a magnetic force.

15. The method of claim 12, wherein at least the first joint is a spherical joint.

16. The method of claim 12, wherein the second joint is located distally from the first joint and proximally from the end effector.

17. A method of precisely positioning an end effector, the method comprising:

providing a device having a base, a first joint and a second joint, each of the first and second joints located distally from the base, and an end effector located distally from the first and second joints, wherein the second joint is located distally from the first joint and proximally from the end effector, the first and second joints each having two portions separated by a gas cushion, the first and second joints allowing the end effector to be movable with respect to the base;

manually positioning the end effector; and removing the gas cushion to cause the two joint portions of each of the first and second joints to contact each other, thereby locking the end effector in the precise location in which it was positioned, wherein the positioning and removing steps comprise positioning the end effector in a relatively coarse manner, removing the gas cushion from the first joint to lock in the relatively course position of the end effector, then positioning the end effector in a relatively fine manner, and then removing a gas cushion from the second joint to lock in the relatively fine position of the end effector.

18. The method of claim 12, further comprising the step of removably attaching the base of the device to a bone of a patient.

19. A positioning system comprising:

a base;

a manually movable end effector;

a first joint, a second joint, and a plurality of links, each interposed between the base and the end effector;

wherein the second joint is interposed between the base and the end effector in parallel with the first joint, wherein each of the plurality of links which may be connecting the first joint to the base and to the end effector have a fixed length to keep a fixed distance between the first joint and any adjacent joint, the base or the end effector, wherein each of the plurality of links which may be connecting the second joint to the base and to the end effector have a fixed length to keep a fixed distance between the second joint and any adjacent joint, the base or the end effector, the first joint and the second joint each comprising a proximal portion and a distal portion coupled together by magnetic attraction and configured to be intermittently separated by a pressurized gas cushion, the first joint and the second joint each configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded, wherein the system is configured such that the end effector moves no more than about 10 microns when the first and the second joints are both changed between the movable state and the fixed state.

20. The system of claim 1, wherein at least one of the joints comprises a ferromagnetic liner configured to reduce a reluctance of a magnetic circuit formed between the proximal portion and the distal portion of the joint.

21. A positioning system comprising:
a base;
a manually movable end effector; and
a first joint and a second joint, each interposed between the base and the end effector, the first joint and the second joint each comprising a proximal portion and a distal portion coupled together by magnetic attraction and configured to be intermittently separated by a pressurized gas cushion, the first joint and the second joint each configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded,
wherein at least one of the joints comprises a roughened contact surface on one or both of the proximal and distal portions of the joint.

22. The system of claim 1, further comprising a foot pedal for controlling the change between the movable state and the fixed state of at least one of the first and second joints.

23. The system of claim 1, wherein the first and second links are immediately adjacent the first joint and the third and fourth links are immediately adjacent the second joint.

24. The system of claim 1, wherein the first and third links are movable with respect to the base, and the second and fourth links are movable with respect to the end effector.

25. The system of claim 24, further comprising:
a third joint located between the first link and the base;
a fourth joint located between the second link and the end effector;
a fifth joint located between the third link and the base; and
a sixth joint located between the fourth link and the end effector.

26. The system of claim 25, wherein at least one of the third, fourth, fifth and sixth joints comprises a proximal portion and a distal portion coupled together by magnetic attraction and configured to be intermittently separated by a pressurized gas cushion, the at least one joint configured to be changeable between a movable state in which the proximal and distal portions are separated by the pressurized gas cushion and movable relative to each other in at least two degrees of freedom, and a fixed state in which the proximal and distal portions contact each other and relative movement is thereby impeded.

27. The system of claim 26, further comprising a sphere member that serves as a common proximal portion for the third and fifth joints, and wherein the third and fifth joints each comprise a distal portion coupled to the sphere member by magnetic attraction and configured to be intermittently separated therefrom by a pressurized gas cushion.

* * * * *